(12) United States Patent
Ou et al.

(10) Patent No.: US 11,666,681 B2
(45) Date of Patent: Jun. 6, 2023

(54) ABRADABLE THERAPEUTIC COATINGS AND DEVICES INCLUDING SUCH COATINGS

(71) Applicant: Ethicon, Inc., Somerville, NJ (US)

(72) Inventors: Duan Li Ou, Warren, NJ (US); Robert J. Tannhauser, Bridgewater, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 0 days.

(21) Appl. No.: 16/102,159

(22) Filed: Aug. 13, 2018

(65) Prior Publication Data

US 2020/0046873 A1 Feb. 13, 2020

(51) Int. Cl.

| A61L 31/12 | (2006.01) |
|---|---|
| A61L 17/00 | (2006.01) |
| A61L 17/14 | (2006.01) |
| A61L 31/10 | (2006.01) |
| A61L 31/16 | (2006.01) |
| A61L 31/06 | (2006.01) |

(52) U.S. Cl.
CPC ............ *A61L 17/145* (2013.01); *A61L 17/005* (2013.01); *A61L 31/06* (2013.01); *A61L 31/10* (2013.01); *A61L 31/125* (2013.01); *A61L 31/16* (2013.01); *A61L 2300/202* (2013.01); *A61L 2300/404* (2013.01); *A61L 2300/606* (2013.01); *A61L 2420/04* (2013.01)

(58) Field of Classification Search
CPC ............ A61L 17/005; A61L 2300/404; A61L 17/145; A61L 2400/18; A61L 2300/606; A61L 2420/00; A61L 2/232; A61L 2420/08; A61L 2300/406; A61L 31/10; A61L 15/28; A61L 27/20; A61L 31/042; A61L 26/0023; A61L 2420/06; A61L 2420/02; A61B 17/0616; A61B 17/0644; A61B 17/06166; A61B 17/04; A61B 17/06066; A61B 17/0469; A61B 17/06; A61K 9/0021; A61K 9/0024; A61P 17/02; A61P 31/04; A61P 31/00; A61F 2220/0075; A61F 2310/0097; A61F 13/0063

See application file for complete search history.

(56) References Cited

U.S. PATENT DOCUMENTS

| 5,380,780 | A | 1/1995 | Olson |
|---|---|---|---|
| 6,620,194 | B2 | 9/2003 | Ding et al. |
| 6,981,944 | B2 | 1/2006 | Jamiolkowski et al. |
| 7,513,093 | B2 | 4/2009 | Scalzo et al. |
| 8,808,724 | B2 | 8/2014 | Cichocki et al. |
| 8,883,245 | B2 | 11/2014 | Cichocki et al. |
| 9,434,857 | B2 | 9/2016 | Ou |
| 2003/0114882 | A1* | 6/2003 | Roby ............... A61L 31/10 606/222 |
| 2003/0236552 | A1 | 12/2003 | Roby |
| 2006/0246208 | A1 | 11/2006 | Mansouri et al. |
| 2007/0010856 | A1* | 1/2007 | Cohen ............... A61L 17/005 606/228 |
| 2007/0299409 | A1 | 12/2007 | Whitbourne et al. |
| 2013/0122314 | A1* | 5/2013 | Ou ............... C09D 183/04 428/429 |
| 2014/0257234 | A1 | 9/2014 | Ma |
| 2014/0357975 | A1 | 12/2014 | Nesbitt |
| 2015/0157319 | A1 | 6/2015 | Thomas et al. |
| 2017/0014364 | A1* | 1/2017 | Hoffmann ............... A61L 27/54 |
| 2018/0163090 | A1 | 6/2018 | Ou |

FOREIGN PATENT DOCUMENTS

| WO | WO-2006088288 A1 * | 8/2006 | ............ A61M 5/329 |
|---|---|---|---|
| WO | 2012174054 A1 | 12/2012 | |

OTHER PUBLICATIONS

Merriam-Webster. Slough. Retrieved on May 11, 2020. <https://www.merriam-webster.com/dictionary/slough>. (Year: 2020).*
Office Action for related European Patent Application No. 19849344.7-1109, dated Apr. 8, 2022, 7 pages.
Chen et al., "Rapid kinetics to peak serum antibodies is achieved following influenza vaccination by dry-coated densely packed microprojections to skin", Journal of Controlled Release, vol. 158, No. 1, Oct. 29, 2011, pp. 78-84.
Office Action for related Indian Patent Application No. 202117004766, dated Nov. 23, 2022, 5 pages.
International Search Report for related International Patent Application No. PCT/IB19/56619, dated Dec. 17, 2019, 5 pages.

* cited by examiner

*Primary Examiner* — Tracy Liu

(57) ABSTRACT

A method of reducing surgical site infection (SSI), using a coated medical device having a tissue penetrating surface and an abradable coating on the medical device comprising at least one antimicrobial agent in the coating.

13 Claims, 3 Drawing Sheets

ABRADABLE THERAPEUTIC COATINGS AND DEVICES INCLUDING SUCH COATINGS

FIELD

Disclosed herein are abradable therapeutic coatings for medical devices having tissue penetrating edges.

ENVIRONMENT

Each year, patients undergo a vast number of surgical procedures worldwide. In the United States, current data shows about twenty-seven million procedures are performed per year. Post-operative or surgical site infections ("SSIs") occur in approximately two to three percent of all cases. This amounts to more than 675,000 SSIs each year.

The occurrence of SSIs is often associated with bacteria that colonize wounds sites subsequent to surgery. During a surgical procedure, bacteria from the surrounding atmosphere may enter the surgical site and deposit in the wound. Additionally, bacteria can be spread during repeated opening and closing of the wound site when changing dressings or the like. Such bacterial contamination of the wound may lead to infection of and trauma to the patient. Accordingly, SSIs may significantly increase undesirable outcomes and the cost of treatment to patients.

There is a need to deliver antimicrobial agents during tissue suturing, using both resorbable and non-resorbable sutures. The current standard of care involves coating or impregnating the suture with triclosan, albeit other agents are suitable, such as chlorhexidine, polyhexamethylene biguanide (PHMB), octenidine, silver, etc. Sutures then release the antimicrobial agents into the surrounding tissue over an extended period of time. While incorporating antimicrobial agents into the suture is highly advantageous, there are some disadvantages that need to be addressed.

Firstly, some sutures are not easily coated with antimicrobial agents, and do not readily incorporate some antimicrobial agents. Various suture coatings can be utilized to then incorporate medically useful agents, such as triclosan, in these coatings. Uniform applications of such coatings to sutures can be technically challenging.

Secondly, medically useful agents can be released from such sutures and coatings with some significant delay, i.e. over a period of days or weeks. While advantageous in some applications, it could also be important to supply high antimicrobial agent concentrations during suturing and immediately thereafter, to combat potential contamination and microbial growth during and immediately after surgery.

There is a need to deliver antimicrobial agents which are bioavailable immediately during suturing and are not dependent on the nature of the suture material.

SUMMARY

Presented herein is a coated medical device, having a tissue penetrating surface and an abradable coating on the medical device comprising at least one antimicrobial agent in the coating.

In one form, the abradable coating is a biocompatible polymer and the antimicrobial agent is incorporated with the biocompatible polymer.

In another form, the biocompatible polymer is not crosslinked and is disposed on the medical device as a sacrificial coating, which is subject to depositing on and/or in a tissue upon penetrating the tissue.

In another form, the abradable coating is coated on only a portion of the medical device.

In yet another form, the antimicrobial agent is selected from the group consisting of halogenated hydroxyl ethers, acyloxydiphenyl ethers, chlorhexidine, polyhexamethylene biguanide (PHMB), octenidine, silver and combinations thereof, such as wherein the antimicrobial agent is triclosan.

In one form, the medical device is a suture needle with an attached suture material, and optionally, the abradable coating is coated on only a portion of the suture needle.

In another form, the medical device is a trocar and the abradable coating is coated on only a tissue penetrating portion of the trocar.

In some forms, the biocompatible polymer has an average molecular weight, Mw, selected to result in abradability of the coating upon passing through tissue.

In another form, at least a portion of the medical device is coated with a lubricious polymer, and the abradable coating is coated on the lubricious polymer.

In this form, the lubricious polymer is less abradable than the abradable coating.

In another form, the lubricious polymer is a polysiloxane.

Advantageously, the abradable coating is soluble in water.

In yet another form, at least a portion of the medical device is coated with a first crosslinked polysiloxane, and the abradable coating is coated on the first crosslinked polysiloxane.

Advantageously, the first crosslinked polysiloxane is the product of a vinyl-terminated polydimethylsiloxane which is crosslinkable with heat or irradiation.

In another form, the abradable coating is a non-crosslinked polysiloxane, or the abradable coating is a second crosslinked polysiloxane, which is crosslinked to a lesser degree than the first crosslinked polysiloxane and crosslinking is catalyzed by a Karstedt catalyst.

In another form, either crosslinked polysiloxane is the product of a vinyl-terminated polydimethylsiloxane.

In one form, the abradable coating is a biocompatible polymer selected from the group consisting of polyacrylamide, polyvinylpyrrolidone, polyvinyl alcohol, polyvinylmethylether, polyethylene oxide, polyethylene glycol, and a mixture of any of these.

In another form, the abradable coating further comprises particles of polycaprolactone and/or copolymers thereof.

Also presented herein is a method of reducing surgical site infection (SSI), comprising providing a coated medical device having a tissue penetrating surface, and an abradable coating on the medical device comprising at least one antimicrobial agent in the coating, penetrating a tissue of a surgical site with the tissue penetrating surface, and depositing at least a portion of the abradable coating on and/or in the tissue.

In this form, the abradable coating is a matrix of a biocompatible polymer and the antimicrobial agent incorporated within the matrix.

In another form, the biocompatible polymer is not crosslinked and is disposed on the medical device as a sacrificial coating.

Optionally, the abradable coating is coated on only a portion of the medical device.

In some forms, the antimicrobial agent is selected from the group consisting of halogenated hydroxyl ethers, acyloxydiphenyl ethers, chlorhexidine, polyhexamethylene biguanide (PHMB), octenidine, silver and combinations thereof, such as wherein the antimicrobial agent is triclosan.

In one form, the medical device is a suture needle with an attached suture material, and optionally, the antimicrobial coating is coated on only a portion of the suture needle.

In another form, the medical device is a trocar, and the antimicrobial coating is coated on only a tissue penetrating portion of the trocar.

In yet another form, the biocompatible polymer has an average molecular weight, Mw, selected to result in abradability of the coating upon passing through tissue.

In another form, at least a portion of the medical device is coated with a lubricious polymer, and the abradable coating is coated on the lubricious polymer, and the lubricious polymer can be a polysiloxane.

In another form, at least a portion of the medical device is coated with a first crosslinked polysiloxane, and the antimicrobial agent containing abradable coating is coated on the first crosslinked polysiloxane and is catalyzed by a Karstedt catalyst.

In one form, the abradable coating is a non-crosslinked polysiloxane, or the abradable coating is a second crosslinked polysiloxane, which is crosslinked to a lesser degree than the first crosslinked polysiloxane and is catalyzed by a Karstedt catalyst.

Alternatively, the abradable coating is a biocompatible polymer selected from the group consisting of polyacrylamide, polyvinylpyrrolidone, polyvinyl alcohol, polyvinylmethylether, polyethylene oxide, polyethylene glycol, and a mixture of any of these.

Advantageously, the antimicrobial agent causes a zone of inhibition of microbial growth of at least about 0.1 mm around the penetrated tissue of a surgical site.

Additionally, at least about 50 wt % of the abradable coating is lost after 10 passes through the penetrated tissue, based upon an original weight of the coating, or even at least about 90 wt % of the abradable coating is lost after 10 passes through the penetrated tissue, based upon an original weight of the coating.

BRIEF DESCRIPTION OF THE DRAWINGS

The forms disclosed herein are illustrated by way of example, and not by way of limitation, in the figures of the accompanying drawings and in which like reference numerals refer to similar elements and in which.

DETAILED DESCRIPTION

Figure 1:
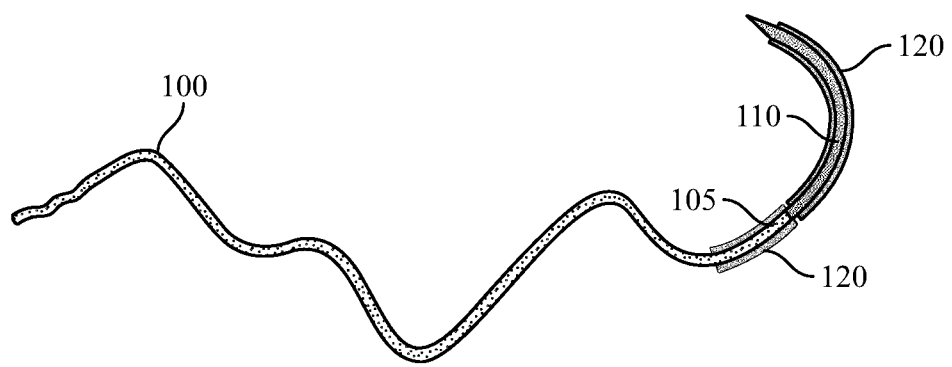
FIG. 1 is a schematic cross-sectional view of a medical device according to the present disclosure, showing a portion of the device coated with an antimicrobial coating.

Described herein is a coated medical device which can help reduce SSIs. The coated medical device has a tissue penetrating surface; and an abradable coating incorporating at least one antimicrobial agent with or in the coating. The antimicrobial agent is generally distributed homogeneously throughout the coating, but could be otherwise distributed, such as along the coating or the like, and still be within the scope of this disclosure.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein, and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

According to the present disclosure, an abradable, weakly cross-linked or non-cross-linked, easy-to-shed coating, and optionally a lubricious coating are applied to a tissue penetrating surface, such as a suture needle surface, or a hypodermic needle surface or a trocar surface, or even to medical devices without tissue penetrating surfaces, such as indwelling catheters, stents, screws, and the like. Alternatively, the abradable coating can be applied to a small portion of a suture immediately adjacent to the suture needle. The abradable coatings contain medically useful agents in the form of compounded or dissolved matter, particles, microparticles, etc. The abradable coatings can be absorbable, non-absorbable, soluble, etc.

The abradable coating can be a biocompatible polymer and the antimicrobial agent can be incorporated with the biocompatible polymer. In one form, the biocompatible polymer can be a non-crosslinked polymer and can be disposed on the medical device as a sacrificial coating, which is subject to depositing on and/or in a tissue upon penetrating the tissue. The abradable coating can be coated on only a portion of the medical device, or can be coated on the entire device. For example, the medical device can be a suture needle with an attached suture material, and the abradable coating can be coated on only a portion of the suture needle, such as on a leading portion of the needle. Alternatively, the abradable coating can be coated only on a mid-portion of the suture needle, or on a trailing portion of the suture needle, and/or optionally on a leading portion of the suture itself.

Alternatively, the medical device can be a trocar or a hypodermic needle, with the abradable coating located only on a tissue penetrating portion of the trocar or hypodermic needle.

Biocompatible polymers suitable to form the abradable coating can be silicone-containing polymers, including cross-linkable siloxane polymers which include vinyl-terminated polydialkylsiloxane or vinyl-terminated polyalkylarylsiloxane. Examples include but are not limited to the following: vinyl-terminated siloxane polymers: polydimethylsiloxane, polydiphenylsilane-dimethylsiloxane copolymer, polyphenylmethylsiloxane, polyfluoropropylmethyl-dimethylsiloxane copolymer and polydiethylsiloxane. It can be advantageous to use vinyl-terminated cross-linkable polydimethyl siloxane. In order to be abradable, the cross-linkable polymers of the abradable coating should be only slightly cross-linked, or even non-crosslinked. Reference is made to U.S. Pat. Nos. 9,434,857, 8,883,245, U.S. Patent Application Publication Nos. 2018/0163090 and 2013/0122314, which are incorporated by reference herein in their entirety, which disclose suitable cross-linkable siloxane polymers (or a mixtures of cross-linkable siloxane polymers and non-cross-linkable siloxane polymers), conventional silicone cross-linking agents, and platinum catalysts. The silicone polymer components are blended with conventional aromatic organic solvents, including, for example, xylene and aliphatic organic solvents (such as, for example, hexane or its commercial derivatives) to form coating solutions or compositions. The cross-linkable siloxane polymers useful in the coating compositions have reactive functionalities or terminal functional groups, including but not limited to vinyl terminated, hydroxyl and acrylate functional groups.

The cross-linking agents that can be used in the include conventional silicone cross-linking agents such as, for example, polymethylhydrosiloxane, polymethylhydro-co-polydimethylsiloxane, polyethyhydrosiloxane, polymethylhydrosiloxane-co-octylmethylsiloxane, and polymethylhydrosiloxane-co-methylphenylsiloxane. The cross-linking agents will have a functionality such as hydrosilyl (—SiH, commonly referred as hydride functions). One advantageous conventional catalyst for use in the coatings of the present invention is polymethylhydrosiloxane.

Further, the abradable coating can be formed from non-cross-linkable siloxanes including polydimethylsiloxane, and polyalkylmethylsiloxanes, such as polydiethylsiloxane, polyfluoropropyl-methylsiloxane, polyoctylmethylsiloxane, polytetradecyl-methylsiloxane, polyoctadecylmethylsiloxane, and polyalkylmethyl-dimethylsiloxanes, such as polyhexadecylmethylsiloxanedimethyl siloxane.

Alternatively, the abradable coatings can be non-silicone based polymers, which are bioabsorbable and/or soluble coatings. Reference is made to U.S. Pat. No. 6,981,944 to Jamiolkowski, et al., incorporated by reference herein in its entirety, which discloses implantable surgical meshes having lubricious coatings. The lubricious coatings therein can be selected from the group consisting polyacrylamide, polyvinylpyrrolidone, polyvinyl alcohol, polyvinylmethylether, polyethylene oxide, polyethylene glycol, and a mixture of any of these.

In any event, the biocompatible polymer can have an average molecular weight, Mw, selected to result in abradability of said coating upon passing through tissue. It can be advantageous if the abradable coating is soluble in water.

Figure 2A:
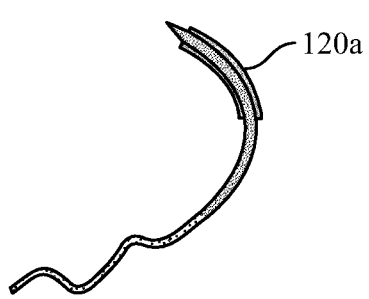
FIGS. 2A to 2C show alternative antimicrobial coating locations from that of FIG. 1.
Figure 2B:
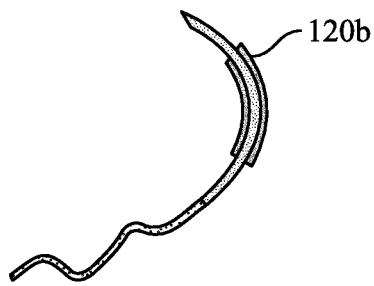
Figure 2C:
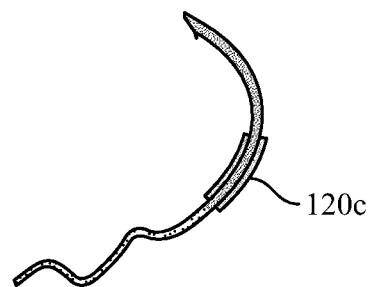

FIG. 1 shows a suture 100 attached to suture needle 110 having the abradable coating 120 on both the whole needle body and on a leading portion 105 of suture 100, with the leading portion 105 being a portion of suture 100 immediately adjacent needle 110, the leading portion 105 having length of from a fraction of the needle length to about three lengths of the needle 110, such as 0.25, 0.5, 1.0, 1.5, 2.0 of the length of needle 110. In some embodiments, leading portion 105 of suture 100 has a coated length of about 5, about 10, about 15, about 20, about 25, or about 30 mm. In one form, abradable coating 120 is applied on both the whole needle 110 body and on the leading portion 105 of the suture 100. In another form, abradable coating 120 is applied on the whole needle 110 body and not on any portion of suture 100. In yet another form, abradable coating 120 is applied only on leading portion of suture 100 and none is applied on the needle 110. FIGS. 2A through 2C show varying locations where the abradable coating can be suitably located. In FIG. 2A, the abradable coating 120a is located on the leading portion of the needle, while in FIG. 2B the abradable coating 120b is located on a mid-portion of the needle. In FIG. 2C the abradable coating 120c is located on the trailing portion of the needle.

According to this disclosure, during suturing the abradable coating is abraded or shed from the device due to interactions with the tissue which is penetrated and is released into the tissue with each needle pass through the tissue, such that a portion of the coating is left in the tissue with each pass through the tissue. An antimicrobial agent, described below is incorporated into the abradable coating and is released into the tissue with portions of the coating, staying in the tissue and providing infection control. As the needle passes through tissue, it sheds the coating and deposits a small quantity of the antimicrobial agent in the tissue. Such release of the antimicrobial agent can be instead of or in addition to any antimicrobial agents released by the suture itself.

Suitable antimicrobial agents can be those which can be homogenously distributed throughout the polymer matrix of the abradable coating. For example, the antimicrobial agent can be any medicant having antibiotic or antimicrobial function, including chlorhexidine, polyhexamethylene biguanide (PHMB), octenidine, silver particles, triclosan, etc.). In one form, particles of a material having high affinity for the antimicrobial agent can be distributed throughout the polymer matrix. For example, it is known that polycaprolactone and co-polymers based on polycaprolactone have a high affinity for triclosan. Thus, particles of (co)polymers of polycaprolactone can be included in the abradable coating when triclosan is selected as the antimicrobial agent.

Figure 3A:
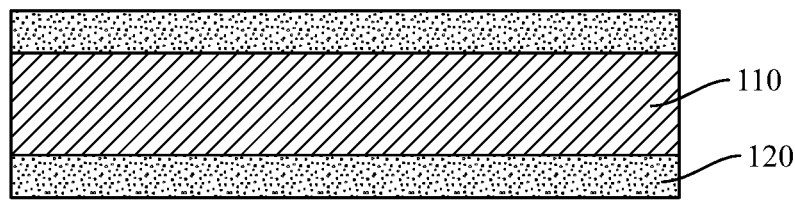
FIGS. 3A and 3B show cross-sectional view of an antimicrobial coated medical device prior to use and after use, respectively.
Figure 3B:
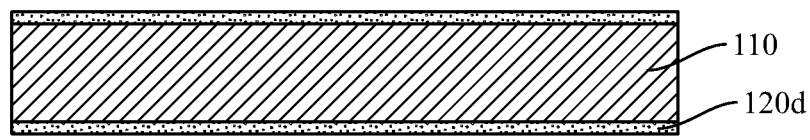

FIGS. 3A and 3B schematically illustrate how the abradable coating 120 is abraded 120d during suturing, showing a schematic cross-sectional view of needle 110 with coating

120. It is shown that after passing through tissue, the thickness of abradable coating 120*d* is decreased due to shedding of a portion of coating 120. The abraded or shed portions of the coating are deposited onto and/or into the tissue.

In one form, the abradable coating can be applied directly to the tissue penetrating surface of the medical device, or can be applied over a conventional lubricious coating 115 (FIG. 4) on the tissue penetrating surface. In this second form, the abradable coating is weaker or less resilient than the underlying lubricious coating 115, such that upon penetrating the target tissue, at least a portion of the abradable coating is released onto and/or into the tissue. In either form, the antimicrobial agent in the abradable coating provides immediate protection against SSIs at that location. In this embodiment, the underlying lubricious coating 115 is sandwiched between the surface of needle 110 and abradable coating 120, with lubricious coating 115 having higher strength and/or structural integrity and/or level of crosslinking than abradable coating 120.

Figure 4:
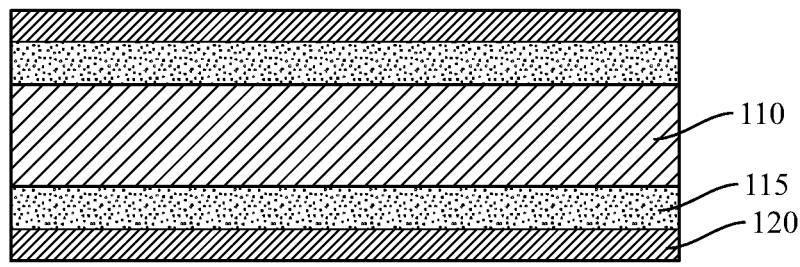
FIG. 4 shows a cross-sectional view of a medical device having multiple coatings.

In the case of a multi-layer coating, shown in FIG. 4, the coating comprises a base lubricious coating 115, for example a silicone-based composition, such as a polysiloxane (e.g., polydimethylsiloxane), which incorporates no antimicrobial agent, or incorporates only a small quantity of the antimicrobial agent that does not substantially change the properties of the coating. In some forms, base lubricious coating 115 contains from about 0 wt % to about 20 wt % of the antimicrobial agent, such as about 0 wt % or about 5 wt %, or about 10 wt %, or even about 15 wt %. The base coating is applied directly to the needle 110 surface. The second layer or sacrificial and abradable coating 120 is applied over the base layer and incorporates a substantial or major quantity of the antimicrobial agent, advantageously homogeneously distributed throughout the second layer.

The antimicrobial agent, described above, can be included in the second abradable or sacrificial antimicrobial coating, which can be a silicone-based composition similar to the base layer, in amounts of from about 5 wt % to about 90 wt %, or more typically from about 25 wt % to about 75 wt %, or even from about 40 wt % to about 60 wt % of the silicone-based composition. The sacrificial coating is formulated so as to be more easily releasable or abradable from the needle than the base coating during suturing i.e. during pulling the needle through the tissue.

According to one form, the formulation of the abradable antimicrobial coating is similar to the base silicone coating, except for its catalyst package, which is a traditional Karlstedt catalyst, with the formulation containing a large amount of the antimicrobial agent, such as about 20-80 wt % of antimicrobial agent. An example of antimicrobial agent is triclosan. Surprisingly and unexpectedly, triclosan acts as an inhibitor for the Karstedt catalyst. The inhibiting effect of triclosan creates a workable coating solution, otherwise this catalyst will cause the solution to gel within minutes.

In another form, the formulation is similar to the base coating, but contains less cross-linker, such as from no cross-linker to from about 0.01 to about 0.5 fraction of cross-linker in the base coating, such as about 0.0, about 0.05 or even about 0.10 fraction of cross-linker relative to that in the base coating. In this case, if the base coating contains 5 wt % cross-linker, the abradable coating contains no cross-linker, or from about 0.25 wt %, or about 0.5 wt % of cross-linker, thus making a weaker coating.

In some forms, the abradable coating is formulated exactly as the base coating, with all the same ingredients, but with the addition of the aforementioned large quantities of the antimicrobial agent(s). In another form, the abradable coating contains a higher percentage of a non-crosslinkable component. According to yet another form, the base coating can be irradiated with gamma irradiation to effect crosslinking and form a highly stable base coating, which is then overcoated by the abradable coating.

Both abradable and base coatings can be applied in a conventional manner such as by dipping, spraying, brushing, etc. After application of the one or more coatings in a uniform manner, the needles (or sutures) are moved into appropriate curing equipment, such as an oven, for a coating curing process wherein energy (e.g., thermal) is provided to cure the coatings. A number of conventional, biocompatible silicone lubricants are known, and they are typically silicone (e.g., polydimethylsiloxane) or silicone-containing coatings. For example, condensation-cured silicone coatings are known to be useful as lubricious coatings on medical devices. Such coating formulations contain amino and alkoxyl functional groups, which can be cured (cross-linked) at relatively low temperatures and high humidity levels. It is also known to use an aminopropyl-containing silicone as a lubricious coating for syringe needles. Those coatings use an epoxy-containing silicone as a cross-linking agent and may have improved penetration performance with multiple penetrations. It is also known to utilize thermoplastic polymers such as polypropylene (e.g., in powder form) in blends of silicone solutions to improve the mechanical properties of the resulting coating layers. The polypropylene powders may increase the durability of silicone needle coatings without sacrificing lubricity. In another form, the antimicrobial can be deposited on the abradable or sacrificial coating by vapor deposition, such as is described in U.S. Pat. No. 7,513,093, incorporated herein by reference in its entirety.

In one form, particles such as silver particles having sizes from about 0.1 micron to about 300 microns, such as about 10, about 50, about 100, or even about 150 microns, are incorporated in a non-soluble abradable coating based on e.g. polydimethylsiloxane, or into a soluble abradable coating such as polyvinylpyrrolidone, polyvinyl alcohol, polyethylene oxide, polyethylene glycol, and a mixture of any of these, in concentrations from about 1% to about 75% by volume, such as from about 2, 3, 5, 10, 15, 20, 30, or 50% by volume. In some forms, silver salts can be used, such as carbonates, lactides, nitrates, or similar.

Figure 5A:
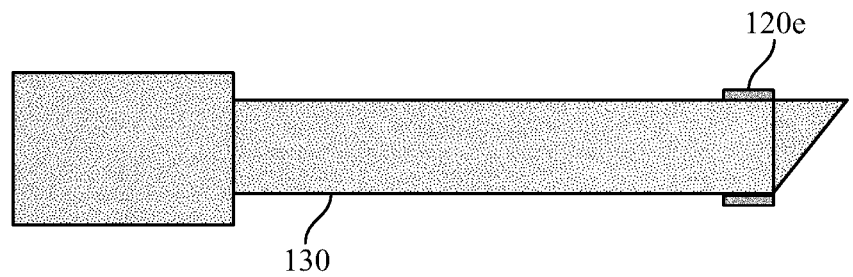
FIGS. 5A and 5B show cross-sectional views of trocars having varying antimicrobial coating extents thereon.
Figure 5B:
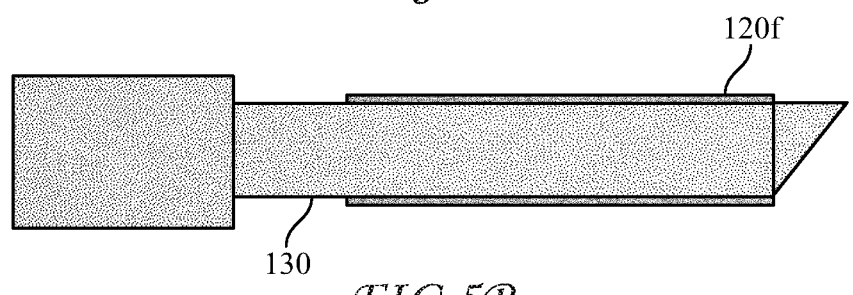

As shown in FIG. 5A a trocar 130 with its cutting edge and its immediate vicinity are coated with abradable coating 120*e*. In FIG. 5B the whole trocar penetration surface is coated with the abradable coating 120*f*.

Figure 6A:
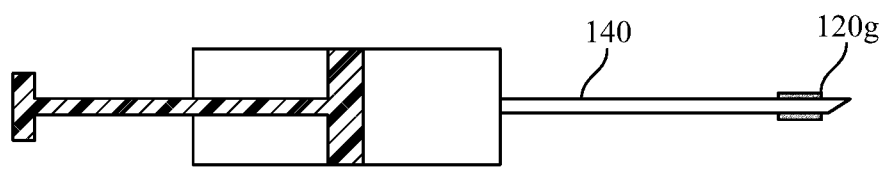
FIGS. 6A and 6B show cross-sectional views of hypodermic needles having varying antimicrobial extents thereon.
Figure 6B:
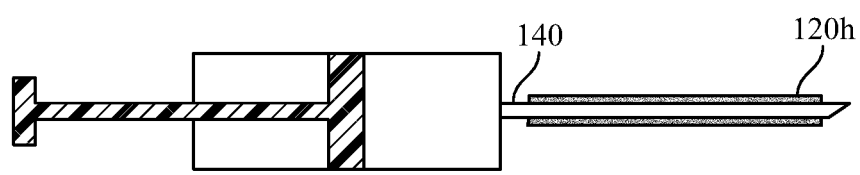

As shown in FIG. 6A, a hypodermic needle 140 with its cutting edge and its immediate vicinity are coated with 120 g of an abradable coating, or as shown in FIG. 6*b*, the whole hypodermic needle penetration surface (or most of the surface) is coated with 120 g of the abradable coating.

The abradable coatings of the present invention are formulated to shed the material of the coating into tissue (and the antimicrobial agent contained therein) during passage through tissues. In some embodiments, at least about 5 wt % of the abradable coating is shed or sloughed off during each passage through tissue, whereby such passage through tissue is defined as passing once though 10 mm layer of tissue. In alternative embodiments, at least about 10 wt %, about 25 wt %, or about 50 wt % of the abradable coating is shed or sloughed off during each passage through tissue. In some forms, the abradable coating is substantially all shed or sloughed off after several passages, such as after 1, 2, 4, 6, 8, 12, 20, 30, or 50 passages through tissue, more preferably after 5 or 10 or 20 passages. Substantially all shed or sloughed off is defined as over about 75%, such as about 80%, about 90%, about 95%, or even about 100% of the abradable coating is removed from the surface of the needle and/or leading portion of the suture.

In all forms, the underlying base lubricious coating, if any, remains substantially intact or exhibits only a minor loss during each passage through tissue, such as the base or lubricious coating losing only about 0 wt %, about 3 wt %, about 5 wt %, or even about 10 wt % during each passage through tissue.

When the abradable coating is applied onto a trocar and/or hypodermic needle, with use of such device typically entailing one insertion into and one removal from the tissue, the abradable coating is formulated to be shed or sloughed off at from about 20-100 wt % during the full cycle involving insertion and removal. For example, upon insertion about 25-50 wt. % is shed, and upon removal about 25-50% is shed. In some forms, only from about 0-30 wt % of the abradable coating is shed upon insertion, and then after exposure to tissue and associated fluids, upon removal a much larger portion of abradable coating is shed, such as from about 50-100 wt %.

In some forms, the weight of the base lubricious coating is from about 0.1 mg to about 5 mg, such as about 1 mg. The weight percentage of the antimicrobial agent in the abradable coating can be from about 20% to about 80%, such as about 50%. The amount of antimicrobial agent released into the tissue during suturing, assuming all of the abradable coating is released can be from about 0.02 mg to about 2.4 mg, such as about 0.5 mg. A few prophetic ranges of expected coatings amounts are shown below in Table 1.

TABLE 1

| Weight of base lubricious coating on the needle, mg | Weight of releasable sacrificial medicated coating, mg | Percentage of the agent in the sacrificial medicated coating | Amount of agent released into the tissue during suturing assuming all sacrificial medicated coating is released |
|---|---|---|---|
| 1 mg | 1 mg | 50% | 0.5 mg |
| 1 mg | 0.5 mg | 50% | 0.25 mg |
| 1 mg | 1 mg | 25% | 0.25 mg |
| 0.5 mg | 1 mg | 50% | 0.5 mg |
| 0.5 mg | 0.5 mg | 50% | 0.25 mg |
| 0.5 mg | 0.25 mg | 50% | 0.125 mg |
| 2 mg | 3 mg | 50% | 1.5 mg |

Example

In order to simulate suturing of an incision, a triclosan containing silicone layer was coated onto 50 mil diameter CTX 420 stainless steel needles, which were pre-coated with a platinum cured silicone in a manner described in Example 5 of U.S. Pat. No. 9,434,857, which is incorporated by reference herein in its entirety for all purposes. The composition of the triclosan-containing silicone coating solution is summarized in Table 1a below. These pre-coated 50 mil CTX needles were fixed onto a strip and coated with a heptane solution, summarized in Table 1A, which contained 14.2 wt % silicone and 3.55 wt % triclosan. This large size needle was used in order to collect enough dose on the penetration media. The coated needles were cured at 70° C. for 3 hr. Total solids content of the solution was about 17.75%, of which 20% by weight was triclosan, resulting in about 20% of final coating by weight being triclosan.

TABLE 1A

Formulation for abrasive coating

| Component | Trade Name | Weight (g) |
|---|---|---|
| Trimethylsilyl terminated polydimethylsiloxane | Gelest DMS-T53 | 1144 |
| Dimethylvinyl silyl terminated polydimethylsiloxane | Gelest DMS-V52 | 1144 |
| Karlstedt Catalyst | Gelest SIP6831.2 | 2.29 |
| Trimethylsilyl terminated polymethylhydrosiloxane | Gelest DMS HMS-991 | 22.9 |
| Triclosan | BASF Irgacare ® MP | 572 |
| Solvent 1 | VWR Xylene | 5087.4 |
| Solvent 2 | VWR Heptane | 8144 |

A penetration test media which was a ⅟₁₆ inch natural gum rubber media sheet was purchased from Rubber Cal Corporation, Calif. The triclosan-coated needle was passed through the test media up to 20 times. The needle penetrated areas from $1^{st}$, $5^{th}$, $10^{th}$ and $20^{th}$ pass penetrations were cut out for a zone of inhibition (ZOI) test.

The needle penetrated sections which had been cut out were tested for ZOI as to growth of *Staphylococcus aureus* on an agar dish for 1 day. A ZOI was detectable on up to the 20th pass penetration and the results were rather consistent. Table 2 shows ZOI observed and indicates that the abradable coating was shed in a relatively uniform manner from 1 to 20 passes, creating a uniform concentration of antimicrobial agent as indicated by ZOI values.

TABLE 2

| Needle pass | ZOI (mm) S. aureus |
|---|---|
| 1 | 13.5 |
| 5 | 13.6 |
| 10 | 11.8 |
| 20 | 13 |

PCT1. A coated medical device, comprising a tissue penetrating surface; and an abradable coating on the medical device comprising at least one antimicrobial agent in the coating.

PCT2. The coated medical device of paragraph PCT1, wherein the abradable coating is a biocompatible polymer and the antimicrobial agent is incorporated with the biocompatible polymer.

PCT3. The coated medical device of paragraph PCT1 or PCT2, wherein the biocompatible polymer is not crosslinked and is disposed on the medical device as a sacrificial coating, which is subject to depositing on and/or in a tissue upon penetrating the tissue.

PCT4. The coated medical device of any preceding PCT paragraph, wherein the abradable coating is coated on only a portion of the medical device.

PCT5. The coated medical device of any preceding PCT paragraph, wherein the antimicrobial agent is selected from the group consisting of halogenated hydroxyl ethers, acyloxydiphenyl ethers, chlorhexidine, polyhexamethylene biguanide (PHMB), octenidine, silver and combinations thereof, and is preferably triclosan.

PCT6. The coated medical device of any preceding PCT paragraph, wherein the medical device is a suture needle with an attached suture material, and the abradable coating is coated on only a portion of the suture needle, or wherein the medical device is a trocar, and the abradable coating is coated on only a tissue penetrating portion of the trocar.

PCT7. The coated medical device of any preceding PCT paragraph, wherein the biocompatible polymer has an average molecular weight, Mw, selected to result in abradability of said coating upon passing through tissue.

PCT8. The coated medical device of any preceding PCT paragraph, wherein at least a portion of the medical device is coated with a lubricious polymer, and the abradable coating is coated on said lubricious polymer.

PCT9. The coated medical device of paragraph PCT8 paragraph, wherein said lubricious polymer is less abradable than said abradable coating, such as wherein the lubricious polymer is a polysiloxane.

PCT10. The coated medical device of any preceding PCT paragraph, wherein said abradable coating is soluble in water.

PCT11. The coated medical device of any preceding PCT paragraph, wherein the abradable coating is a non-cross-linked polysiloxane.

PCT12. The coated medical device of any preceding PCT paragraph, wherein at least a portion of the medical device is coated with a first crosslinked polysiloxane which is crosslinkable with heat or irradiation.

PCT13. The coated medical device of paragraph PCT12, wherein the abradable coating is a second crosslinked polysiloxane, which is crosslinked to a lesser degree than the first crosslinked polysiloxane and crosslinking is catalyzed by a Karstedt catalyst.

PCT14. The coated medical device of paragraph PCT12 or PCT13, wherein either crosslinked polysiloxane is the product of a vinyl-terminated polydimethylsiloxane.

PCT15. The coated medical device of paragraphs PCT1 to PCT10, wherein the abradable coating is a biocompatible polymer selected from the group consisting of polyacrylamide, polyvinylpyrrolidone, polyvinyl alcohol, polyvinylmethylether, polyethylene oxide, polyethylene glycol, and a mixture of any of these.

PCT16. The coated medical device of any preceding PCT paragraph, wherein the abradable coating further comprises particles of polycaprolactone and/or copolymers thereof.

PCT17. A method of reducing surgical site infection (SSI), comprising: providing a coated medical device having a tissue penetrating surface, and an abradable coating according to any preceding PCT paragraph, on the medical device comprising at least one antimicrobial agent in the coating; penetrating a tissue of a surgical site with said tissue penetrating surface; and depositing at least a portion of said abradable coating on and/or in said tissue.

PCT18. The method of paragraph PCT17, wherein the antimicrobial agent causes a zone of inhibition of microbial growth of at least about 0.1 mm around the penetrated tissue of a surgical site.

PCT19. The method of paragraph PCT17 or PCT18, wherein at least about 50 wt % of the abradable coating is lost after 10 passes through the penetrated tissue, based upon an original weight of the coating.

PCT20. The method of paragraphs PCT17 to PCT19, wherein at least about 90 wt % of the abradable coating is lost after 10 passes through the penetrated tissue, based upon an original weight of the coating.

INDUSTRIAL APPLICABILITY

The systems and methods disclosed herein are applicable to the health care industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

We claim:

1. A method of reducing surgical site infection (SSI), comprising:
   providing a medical device having a tissue penetrating surface, at least a portion of said medical device coated with a lubricious, first cross-linked polysiloxane polymer which is further coated with an abradable, non-crosslinked polysiloxane lubricious coating comprising at least one antimicrobial agent incorporated in a matrix of the non-crosslinked polysiloxane;
   penetrating a tissue of a surgical site with said tissue penetrating surface;
   depositing at least a portion of said abradable lubricious coating on and/or in said tissue,
   wherein said device is a suture needle with attached suture; and
   wherein said method comprises multiple passages through tissue comprising pulling the needle through the tissue followed by said suture and a portion of the abradable lubricious coating sloughs off during each passage through the tissue, wherein each of said passages deposits a portion of said abradable lubricious coating sufficient to generate a zone of inhibition (ZOI) on *Staphylococcus aureus* for 24 hours after said passages.

2. The method of claim 1, wherein the abradable lubricious coating is disposed on the medical device as a sacrificial coating.

3. The method of claim 1, wherein the at least one antimicrobial agent is selected from the group consisting of halogenated hydroxyl ethers, acyloxydiphenyl ethers, chlorhexidine, polyhexamethylene biguanide (PHMB), octenidine, silver and combinations thereof.

4. The method of claim 1, wherein the at least one antimicrobial agent is triclosan.

5. The method of claim 1, wherein the non-crosslinked polysiloxane has a weight average molecular weight, Mw, selected to result in abradability of said coating upon passing through tissue.

6. The method of claim 1, wherein the at least one antimicrobial agent causes a zone of inhibition (ZOI) of microbial growth of at least about 0.1 mm around the penetrated tissue of a surgical site.

7. The method of claim 1, wherein at least about 50 wt % of the abradable lubricious coating is lost after 10 passes through the penetrated tissue, based upon an original weight of the coating.

8. The method of claim 7, wherein at least about 90 wt % of the abradable lubricious coating is lost after 10 passes through the penetrated tissue, based upon an original weight of the coating.

9. The method of claim 1, wherein the multiple passages comprise at least 5 passages and up to 50 passages.

10. The method of claim 1, wherein the multiple passages comprise at least 10 passages and up to 50 passages.

11. The method of claim 1, wherein the multiple passages comprise at least 15 passages and up to 50 passages.

12. The method of claim 1, wherein the multiple passages comprise at least 20 passages and up to 50 passages.

13. The method of claim 1, wherein each of said passages creates a uniform concentration of antimicrobial agent as indicated by zone of inhibition (ZOI).

\* \* \* \* \*